United States Patent
Farnan

(10) Patent No.: US 7,108,684 B2
(45) Date of Patent: Sep. 19, 2006

(54) DRUG DELIVERY BALLOON CATHETER

(75) Inventor: Robert C. Farnan, Davie, FL (US)

(73) Assignee: Novoste Corporation, Norcross, GA (US)

( * ) Notice: Subject to any disclaimer, the term of this patent is extended or adjusted under 35 U.S.C. 154(b) by 0 days.

(21) Appl. No.: 10/749,658

(22) Filed: Dec. 31, 2003

(65) Prior Publication Data

US 2004/0210191 A1    Oct. 21, 2004

Related U.S. Application Data

(60) Provisional application No. 60/437,863, filed on Jan. 2, 2003.

(51) Int. Cl.
*A61M 31/00* (2006.01)
(52) U.S. Cl. ............ 604/509; 604/103.02; 604/103.05; 604/103.07; 606/192; 606/194
(58) Field of Classification Search ............ 604/96.01, 604/264, 507–511, 101.04, 103.02, 103.05, 604/103.07, 103.08, 523, 528, 537, 544, 604/915, 916; 606/192, 194; 623/1.42–1.54, 623/1.11, 1.12
See application file for complete search history.

(56) References Cited

U.S. PATENT DOCUMENTS

| | | | | |
|---|---|---|---|---|
| 5,100,429 A | * | 3/1992 | Sinofsky et al. ............ 623/1.21 |
| 5,116,318 A | * | 5/1992 | Hillstead ................ 604/103.14 |
| 5,286,254 A | | 2/1994 | Shapland et al. |
| 5,318,531 A | | 6/1994 | Leone |
| 5,536,250 A | | 7/1996 | Klein et al. |
| 5,569,184 A | * | 10/1996 | Crocker et al. ............. 604/509 |
| 5,681,281 A | | 10/1997 | Vigil et al. |
| 5,693,085 A | * | 12/1997 | Buirge et al. .............. 623/1.13 |
| 5,792,106 A | * | 8/1998 | Mische ................... 604/103.01 |
| 5,833,659 A | * | 11/1998 | Kranys ..................... 604/97.01 |
| 5,843,116 A | * | 12/1998 | Crocker et al. ............. 606/192 |
| 5,857,998 A | * | 1/1999 | Barry ..................... 604/103.03 |
| 5,876,426 A | | 3/1999 | Kume et al. |
| 5,985,307 A | | 11/1999 | Hanson et al. |
| 6,146,358 A | * | 11/2000 | Rowe ..................... 604/103.02 |
| 6,149,641 A | * | 11/2000 | Ungs .......................... 604/501 |
| 6,280,411 B1 | * | 8/2001 | Lennox ................. 604/103.05 |
| 6,293,959 B1 | * | 9/2001 | Miller et al. ................. 606/194 |
| 6,309,402 B1 | * | 10/2001 | Jendersee et al. .......... 623/1.11 |
| 6,364,856 B1 | | 4/2002 | Ding et al. |
| 6,524,274 B1 | * | 2/2003 | Rosenthal et al. ........ 604/96.01 |
| 6,544,221 B1 | | 4/2003 | Kokish et al. |
| 6,544,223 B1 | * | 4/2003 | Kokish ................... 604/103.01 |
| 6,638,246 B1 | * | 10/2003 | Naimark et al. ............. 604/103 |
| 6,645,135 B1 | * | 11/2003 | Bhat ............................. 600/3 |

(Continued)

OTHER PUBLICATIONS

International Search Report on International application No. PCT/US03/41823; dated Jun. 9, 2004.

*Primary Examiner*—Cris Rodriguez
(74) *Attorney, Agent, or Firm*—Cook, Alex, McFarron, Manzo, Cummings & Mehler, Ltd.

(57) ABSTRACT

The present invention is directed to an apparatus and method for delivering a drug to a selected site in the vascular system of a patient. More specifically, the apparatus is a balloon catheter comprising an expandable balloon with a pouch around at least a portion of the balloon. When the balloon is not expanded, an agent can be located in the area between the pouch and the balloon. The agent is released through the pouch when the balloon is expanded.

12 Claims, 2 Drawing Sheets

U.S. PATENT DOCUMENTS

| | | |
|---|---|---|
| 6,656,155 B1 * | 12/2003 | Freyman ................ 604/103.01 |
| 6,733,474 B1 * | 5/2004 | Kusleika ................ 604/103.01 |
| 6,955,661 B1 * | 10/2005 | Herweck et al. ............ 604/264 |
| 2001/0014821 A1 * | 8/2001 | Juman et al. ............... 623/1.11 |
| 2002/0082552 A1 * | 6/2002 | Ding et al. ............ 604/103.02 |
| 2003/0033001 A1 * | 2/2003 | Igaki ........................ 623/1.11 |
| 2003/0139806 A1 * | 7/2003 | Haverkost et al. ......... 623/1.33 |
| 2003/0181973 A1 * | 9/2003 | Sahota ...................... 623/1.15 |
| 2003/0229307 A1 * | 12/2003 | Muni et al. ............ 604/103.02 |
| 2004/0087902 A1 * | 5/2004 | Richter .................. 604/103.02 |
| 2004/0267356 A1 * | 12/2004 | Scott et al. ................ 623/1.42 |

* cited by examiner

DRUG DELIVERY BALLOON CATHETER

This application is based on provisional application Ser. No. 60/438,863 filed Jan. 2, 2003, which is incorporated herein by reference.

FIELD OF THE INVENTION

The present invention relates generally to the delivery of drugs or therapeutic agents by a catheter to a selected site within the vascular system of a patient. More particularly, the present invention relates to method and apparatus for the delivery of a drug or therapeutic agent to a selected site within the vascular system using a balloon catheter.

BACKGROUND OF THE INVENTION

The vascular system of the human is subject to blockage due to plaque within the arteries. Partial and even complete blockage of arteries by the formation of an atherosclerotic plaque is a well known and frequent medical problem. Frequently, such blockage occurs in the coronary arties. Such blockages may be treated using atherectomy devices, which mechanically remove the plaque; hot or cold lasers, which vaporize the plaque; stents, which hold the artery open; and other devices and procedures which have the objective of allowing increased blood flow-through the artery.

The most common of such procedures is the percutaneous transluminal coronary angioplasty (PTCA) procedure—more commonly referred to as balloon angioplasty. In this procedure, a catheter having an inflatable balloon at its distal end is introduced into the coronary artery, the uninflated balloon is positioned at the stenotic site, and the balloon is inflated. Inflation of the balloon disrupts and flattens the plaque against the arterial wall, and stretches the arterial wall, resulting in enlargement of the intraluminal passageway and increased blood flow. After such expansion, the balloon is deflated, and the balloon catheter removed.

Such a procedure is also used in arteries other than coronary arteries in the vascular system. In such a case, the procedure is referred to as percutaneous transluminal angioplasty (PTA) and is very similar to that described above for PCTA.

During PCTA or PTA, it is desirable to delivery a therapeutic agent or drug to area where the balloon angioplasty is occurring to prevent restenosis, repair vessel dissections or small aneurysms or provide other desired treatment.

Various drug delivery catheters have been developed that allow localized delivery of a therapeutic agent. In these catheters, typically a lumen is provided that allows the physician to deliver the drug to the balloon area of the catheter. There are, however, at least two drawbacks to this type of design. First, localized "jetting" of the drug from the lumen may damage the vessel. Second, there is a general difficulty or inability to control and maintain the drug in the desired treatment location.

SUMMARY OF THE INVENTION

The present invention is directed to method and apparatus for applying an agent, such as a therapeutic agent or drug, to a selected site within the vascular system of a patient. The device comprises a balloon catheter including an elongated catheter shaft expandable balloon and a pouch or sleeve around at least a portion of the balloon. The area between the pouch and balloon is adaptable to receiving an agent, such as a medicament, drug or other therapeutic agent, prior to expansion of the balloon. The agent is releasable through the pouch when the balloon is expanded, such as by the expanding balloon against the pouch, forcing the drug through pores in the pouch. In a further embodiment of the present invention, an agent is located within the area between the pouch and portion of the balloon, prior to expansion of the balloon. Preferably, the expandable balloon has an annular ridge at both the distal and proximal ends of the balloon, and the pouch is located between these annular ridges. In a further embodiment of the present invention, the pouch is made of ePTFE material and/or has a higher burst strength than the expandable balloon.

In still a further embodiment of the present invention, the distal and proximal ends of the expandable balloon have a conical shape which slopes downward from the annular ridges to the respective distal and proximal ends of the balloon. Further, the pouch can be located on a working length of the expandable balloon which is located between the annular ridges and may have a diameter less than the diameter of the annular ridges.

The present invention is also directed to a method for delivery of a therapeutic agent to a selected site within a vascular system of a patient. The method involves providing a balloon catheter embodying the present invention as described above. An agent is loaded into the area between the pouch and the non-expanded balloon. The balloon catheter is then inserted into the patient, and the balloon moved to the selected site within the vascular system. The balloon is then expanded, forcing the agent through the pouch to the selected site in the vascular system. Such method may be used for a variety of treatments and may be used in conjunction with PCTA or PTA.

DETAILED DESCRIPTION OF THE PRESENTLY PREFERRED EMBODIMENT

Figure 1:
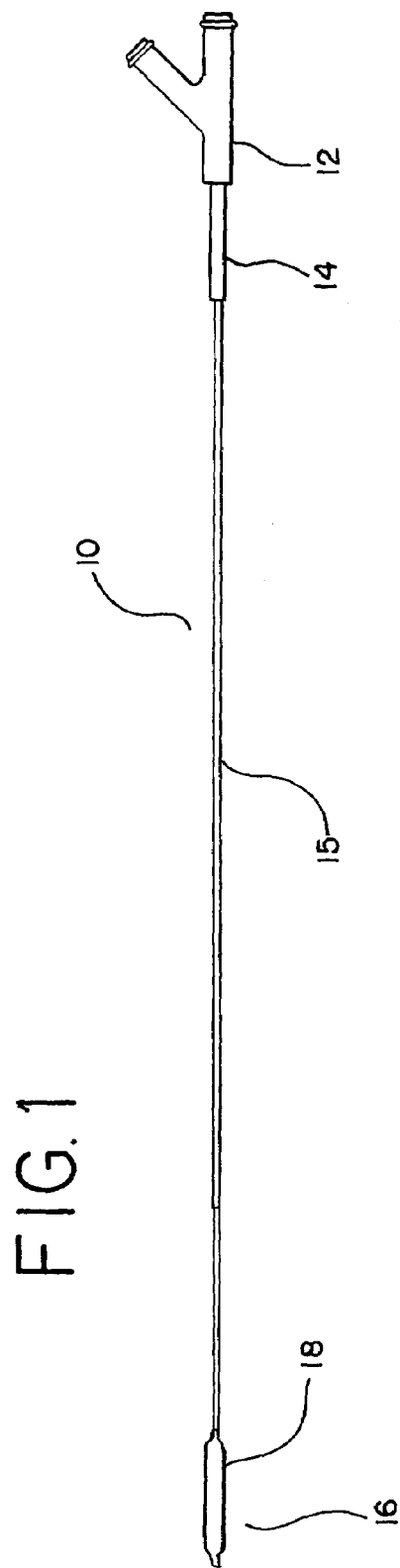
FIG. 1 is a plain view of a balloon catheter embodying the present invention.

FIG. 1 illustrates a balloon type catheter 10 employing the present invention, which may be a PTA or PTCA catheter (dilatation catheter). The catheter has an elongated shaft 15, which may include a plurality of lumens including an inflation lumen and a guide wire lumen arranged side-by-side or coaxially. If coaxial, the catheter shaft may include inner and outer members defining an inner guide wire lumen and a balloon inflation lumen, therebetween. The catheter could also be a rapid exchange catheter. Construction details may vary—each member may have up to 3 layers and can be reinforced with braids, if desired, and tapered at the distal ends The proximal end of the catheter 10 in FIG. 1 has an integrated bifurcated hub 12 for connecting an inflation source, with one strain relief tube 14 extending distally a short distance from the hub. The catheter shaft is built using conventional materials and processes. The catheter shafts may have a diameter ranging from approximately 2.5 F to 8 F. A catheter having multi-durometer tubing with variable stiffness technology is also possible. The catheter is preferably compatible with standard sheaths and guide catheters which are well known in the art. Optionally, the catheter may be a multi-lumen design. The catheter may also have a lumen or lumens that allow for perfusion across the balloon when the balloon is inflated.

Figure 2:
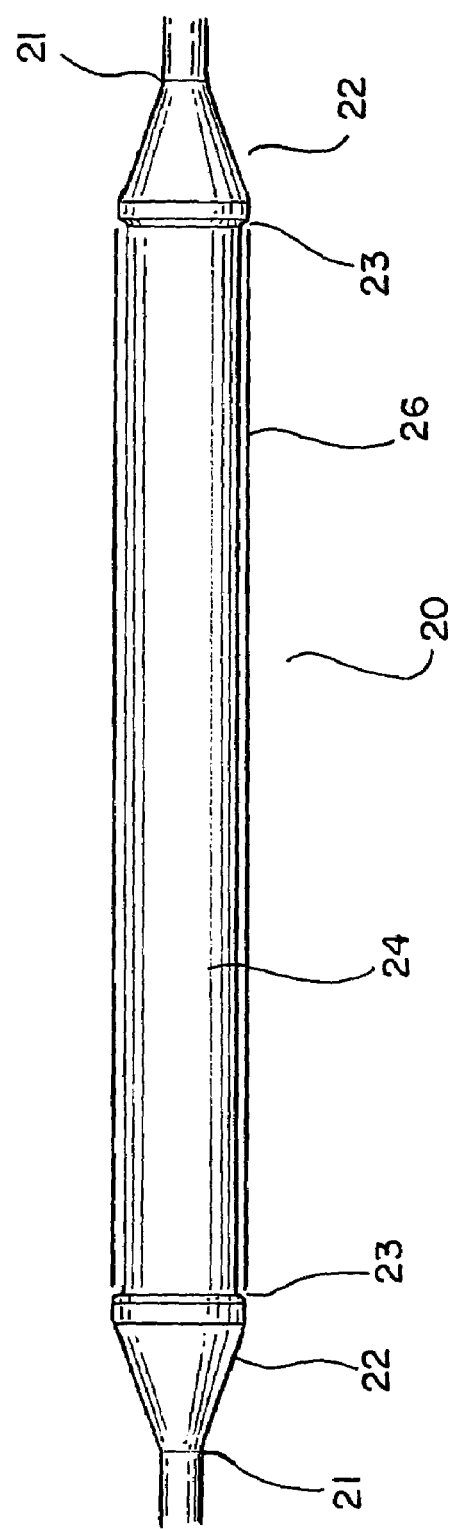
FIG. 2 is a partial cross-sectional of the balloon end of a catheter embodying the present invention.

The present invention embodies a novel distal end assembly for local drug, "gene", or other type of therapy. FIG. 2 depicts an embodiment of the distal end of the catheter. The balloon 18 may be made of various materials to exhibit selected properties. For example, the balloon may be made of either nylon or nylon copolymer (compliant, non-puncture) or PET (high pressure, non-compliant) with a urethane, polymer, or other coating known in the art to provide tackiness and/or puncture resistance. The balloon may be a multi-layered balloon with the layers having different compliant characteristics, such as a non-compliant inner layer and a most compliant outer layer. For example, the balloon can include an inner most layer of PET, which provides a higher pressure balloon, surrounded by an outer layer of nylon, which provides a more puncture-resistant surface. The balloon may be from 1.5–12 mm in diameter—for example 1.5–5 mm for coronary vessels and 4–12 mm for peripheral vessels. The balloon may have a length of about 15–120 mm—for example, 5–40 mm length for coronary applications and up to 120 mm length for use in peripheral vessels. The balloon inflation rated pressure will preferably be from 6–20 atmospheres, depending on the wall thickness of the balloon.

The balloon 18 of this embodiment has a "necked" dilatation balloon structure with a cone shape 22 on either end of the balloon. The tip end 21 of cone preferably is adhered to the catheter using conventional attachment means or techniques. The other end of the cone preferably defines an annular ridge 23 which slopes downward to the catheter's/balloon's working length 24, where it is of reduced diameter relative to the diameter of the annular ridge 23 or the widest part of the cone 22.

In accordance with the present invention, a pouch or sleeve may be provided over at least a portion of the balloon. In FIG. 2, a cylindrical ePTFE pouch 26, with WEP characteristics, is provided over the working length of the balloon. The pouch 26 is shown in FIG. 2 in a cross-sectional view. The pouch 26 is preferably a cylindrical membrane and made of ePTFE (ePolytetrafluoroethylene) material which is soft, flexible and has microscopic pores therein. WEP is an industry term used by manufacturers of ePTFE to indicate a material which has known or controllable permeability. Preferably, the pouch 26 is designed to have a higher burst strength than the balloon underneath.

Preferably, the balloon and over-pouch assembly is assembled prior to placing on the dilatation catheter. Once assembled and bonded onto the catheter, the drug or therapeutic agent may be loaded into the annular space between the pouch and balloon. The permeability characteristics of the material in the pouch 26 (e.g., ePTFE) allow the drug or agent to be contained within the pouch until the balloon underneath is expanded to force the drug or agent thru the pores in the pouch material. An alternate approach would be to provide a means for the physician to load the drug immediately before usage. Taxol paclitaxel (trademark of Bristol-Myers Squibb Company) and serolimus rapamycin are examples of two drugs or agents which may be loaded into the pouch for application to the vessel lining.

Once the drug or agent has been loaded into the balloon and the balloon is positioned at the lesion, the balloon would be inflated to perform the primary dilatation of the lesion. While dilating, the drug or agent would be simultaneously released through the pores in the pouch in a dispersed and controlled manner. The rate and quantity of drug/agent release would be directly dependent upon the dilatation pressure and the pore size in the pouch, which may be chosen, as needed for particular agents or treatment regimens. Because no additional time would be involved hooking up syringes and delivering a drug while the balloon is inflated, as in current product designs, perfusion may not be necessary and procedure time minimized. This design allows direct and instantaneous delivery of the drug/therapeutic agent during the primary treatment of the vessel.

It will be understood that the embodiments and examples of the present invention, which have been described, are illustrative of some of the applications of the principles of the present invention. Numerous modifications may be made by those skilled in the art without departing from the true spirit and scope of the invention.

The invention claimed is:

1. A balloon catheter comprising:
   an elongated catheter shaft having proximal and distal end portions;
   an expandable balloon located at the distal end portion of the catheter shaft, the balloon having a distal end and a proximal end; and
   a pouch disposed on at least a portion of said expandable balloon,
   wherein said pouch expands and contracts with said balloon and wherein said balloon and pouch are removable together from a patient,
   wherein an area between said pouch and said portion of said expandable balloon is adaptive to receiving an agent when the balloon is not expanded,
   wherein said agent is releasable through said pouch when said balloon is expanded, and
   wherein said expandable balloon has an annular ridge at both the distal end and proximal end of the balloon, and the pouch is located between the annular ridges.

2. The balloon catheter of claim 1 wherein said pouch has a higher burst strength than said expandable balloon.

3. The balloon catheter of claim 1 wherein said distal and proximal ends of said expandable balloon have a cone shape which slopes downward from said annular ridges to the distal and proximal ends of the balloon.

4. The balloon catheter of claim 1 wherein said pouch is located on a working length of said expandable balloon which is located between said annular ridges and has a diameter less than the diameter of the annular ridges.

5. The balloon catheter of claim 1 wherein said balloon catheter is a percutaneous transluminal coronary angioplasty catheter.

6. The balloon catheter of claim 1 wherein said balloon catheter is a percutaneous transluminal angioplasty catheter.

7. The balloon catheter of claim 1 further comprising an agent disposed between the pouch and the expandable balloon when the balloon is not expanded, wherein said agent is releasable through said pouch when said balloon is expanded.

8. The balloon catheter of claim 1 wherein said pouch is made of epolytetrafluoroethylene (ePTFE) material.

9. A method for delivery of a drug agent to a selected site within a vascular system of a patient comprising:
   providing a catheter comprising an elongated catheter shaft having proximal and distal end portions, an expandable balloon located at the distal end portion of the catheter shaft, the balloon having a distal end and a proximal end, and a pouch disposed on at least a portion of said expandable balloon, wherein said pouch expands and contracts with said balloon, wherein an area between said pouch and said portion of said expandable balloon is adaptive to receiving said agent when the balloon is not expanded, wherein said agent is releasable through said pouch when said balloon is expanded, and wherein said expandable balloon has an annular ridge at both the distal end and proximal end of the balloon, and the pouch is located between the annular ridges;

loading and holding said agent in the area between said pouch and said balloon when the balloon is not expanded;

locating said balloon at said selected site within the vascular system;

expanding said balloon, wherein said agent is released through said pouch to said selected site within the vascular system when said balloon is expanded; and deflating said balloon and removing said deflated balloon and pouch from said patient.

10. The method of claim 9 wherein agent is delivered during percutaneous transluminal coronary angioplasty.

11. The method of claim 9 wherein agent is delivered during percutaneous transluminal angioplasty.

12. The method of claim 9 wherein the pouch of the catheter is made of epolytetrafluoroethylene (ePTFE).

* * * * *